(12) United States Patent
Perry et al.

(10) Patent No.: US 11,051,720 B2
(45) Date of Patent: Jul. 6, 2021

(54) FITNESS TRACKING FOR CONSTRAINED-ARM USAGE

(71) Applicant: Apple Inc., Cupertino, CA (US)

(72) Inventors: Daniel J. Perry, Cupertino, CA (US); Edith M. Arnold, San Francisco, CA (US); Hung A. Pham, Oakland, CA (US); Jonathan M. Beard, Berkley, CA (US); Karthik Jayaraman Raghuram, Mountain View, CA (US); Vinay R. Majjigi, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 332 days.

(21) Appl. No.: 15/611,010

(22) Filed: Jun. 1, 2017

(65) Prior Publication Data

US 2018/0344217 A1  Dec. 6, 2018

(51) Int. Cl.
| | | |
|---|---|---|
| *A61B 5/11* | (2006.01) | |
| *A61B 5/00* | (2006.01) | |
| *G01C 22/00* | (2006.01) | |
| *A61B 5/024* | (2006.01) | |
| *A61B 5/22* | (2006.01) | |

(52) U.S. Cl.
CPC .......... *A61B 5/1123* (2013.01); *A61B 5/0004* (2013.01); *A61B 5/112* (2013.01); *A61B 5/1118* (2013.01); *A61B 5/1121* (2013.01); *A61B 5/681* (2013.01); *G01C 22/006* (2013.01); *A61B 5/0002* (2013.01); *A61B 5/02438* (2013.01); *A61B 5/1112* (2013.01); *A61B 5/22* (2013.01); *A61B 5/4866* (2013.01); *A61B 5/6824* (2013.01); *A61B 2560/0223* (2013.01); *A61B 2562/028* (2013.01); *A61B 2562/0219* (2013.01); *A61B 2562/0247* (2013.01)

(58) Field of Classification Search
None
See application file for complete search history.

(56) References Cited

U.S. PATENT DOCUMENTS

| | | | |
|---|---|---|---|
| 4,566,461 | A | 1/1986 | Lubell et al. |
| 5,158,093 | A | 10/1992 | Shvartz et al. |
| 5,663,897 | A | 9/1997 | Geiser |

(Continued)

FOREIGN PATENT DOCUMENTS

| | | |
|---|---|---|
| AU | 2008100295 A4 | 5/2008 |
| CN | 102481479 A | 5/2012 |

(Continued)

OTHER PUBLICATIONS

International Search Report and Written Opinion received for PCT Patent Application No. PCT/US2018/047290, dated Nov. 8, 2018, 14 pages.

(Continued)

*Primary Examiner* — Matthew Kremer
*Assistant Examiner* — Samuel C Kim
(74) *Attorney, Agent, or Firm* — Fish & Richardson P.C.

(57) ABSTRACT

A system and method for collecting motion data using a fitness tracking device located on an arm of a user, detecting that the arm is constrained based on the motion data, estimating a stride length of the user based on the motion data and historical step cadence-to-stride length data, calculating fitness data using the estimated stride length, and outputting the fitness data to the user.

22 Claims, 10 Drawing Sheets

(56) References Cited

U.S. PATENT DOCUMENTS

| | | |
|---|---|---|
| 5,664,499 A | 9/1997 | Kingsmill |
| 6,013,008 A | 1/2000 | Fukushima |
| 6,059,724 A | 5/2000 | Campell et al. |
| 6,582,380 B2 | 6/2003 | Kazlausky et al. |
| 6,687,535 B2 | 2/2004 | Hautala et al. |
| 6,837,827 B1 | 1/2005 | Lee et al. |
| 6,868,338 B1 | 3/2005 | Elliott |
| 7,254,516 B2 | 8/2007 | Case, Jr. et al. |
| 7,311,675 B2 | 12/2007 | Peifer et al. |
| 7,377,180 B2 | 5/2008 | Cunningham |
| 7,387,029 B2 | 6/2008 | Cunningham |
| 7,467,060 B2 | 12/2008 | Kulach et al. |
| 7,534,206 B1 | 5/2009 | Lovitt et al. |
| 7,647,196 B2 | 1/2010 | Kahn et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,531,180 B2 | 9/2013 | Piemonte et al. |
| 8,589,174 B2 | 11/2013 | Nelson et al. |
| 8,638,320 B2 | 1/2014 | Harley et al. |
| 8,653,956 B2 | 2/2014 | Berkobin et al. |
| 8,784,271 B2 | 7/2014 | Brumback et al. |
| 8,890,854 B2 | 11/2014 | Tenuta et al. |
| 8,892,391 B2 | 11/2014 | Tu et al. |
| 8,894,576 B2 | 11/2014 | Alwan et al. |
| 8,911,329 B2 | 12/2014 | Lin et al. |
| 8,928,635 B2 | 1/2015 | Harley et al. |
| 9,195,305 B2 | 11/2015 | Markovic et al. |
| 9,264,862 B2 | 2/2016 | Tu et al. |
| 9,413,871 B2 | 8/2016 | Nixon et al. |
| 9,448,250 B2 | 9/2016 | Pham et al. |
| 9,526,430 B2 | 12/2016 | Srinivas et al. |
| 9,788,794 B2 | 10/2017 | Le Boeuf et al. |
| 9,918,646 B2 | 3/2018 | Alvarado et al. |
| 9,998,864 B2 | 6/2018 | Kumar et al. |
| 10,098,549 B2 | 10/2018 | Tan et al. |
| 10,154,789 B2 | 12/2018 | Raghuram et al. |
| 10,188,347 B2 | 1/2019 | Self et al. |
| 10,206,627 B2 | 2/2019 | Le Boeuf et al. |
| 10,219,708 B2 | 3/2019 | Altini |
| 10,244,948 B2 | 4/2019 | Pham et al. |
| 10,290,260 B2 | 5/2019 | Wisbey et al. |
| 10,292,606 B2 | 5/2019 | Wisbey et al. |
| 10,512,406 B2 | 12/2019 | Martinez et al. |
| 10,524,670 B2 | 1/2020 | Raghuram et al. |
| 10,620,232 B2 | 4/2020 | Tu et al. |
| 10,687,707 B2 | 6/2020 | Tan et al. |
| 10,687,752 B2 | 6/2020 | Pham et al. |
| 10,694,994 B2 | 6/2020 | Alvarado et al. |
| 10,699,594 B2 | 6/2020 | Mermel et al. |
| 10,617,912 B2 | 7/2020 | Narasimha Rao et al. |
| 10,709,933 B2 | 7/2020 | Tan et al. |
| 2001/0022828 A1* | 9/2001 | Pyles .............. G01C 22/006 377/24.2 |
| 2002/0019585 A1 | 2/2002 | Dickinson |
| 2003/0032460 A1 | 2/2003 | Cannon et al. |
| 2003/0138763 A1 | 7/2003 | Roncalez et al. |
| 2004/0064061 A1 | 4/2004 | Nissila |
| 2005/0107723 A1 | 5/2005 | Wehman et al. |
| 2005/0124906 A1 | 6/2005 | Childre et al. |
| 2005/0212701 A1 | 9/2005 | Nimmo |
| 2006/0064277 A1 | 3/2006 | Jung et al. |
| 2006/0136173 A1 | 6/2006 | Case et al. |
| 2006/0190217 A1 | 8/2006 | Lee et al. |
| 2006/0217231 A1 | 9/2006 | Parks et al. |
| 2007/0100666 A1 | 5/2007 | Stivoric et al. |
| 2007/0150229 A1* | 6/2007 | Fujiwara ............ G01C 22/006 702/160 |
| 2007/0219059 A1 | 9/2007 | Schwartz et al. |
| 2007/0275825 A1 | 11/2007 | O'Brien |
| 2007/0276271 A1 | 11/2007 | Chan |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1 | 1/2009 | Karlov et al. |
| 2009/0043531 A1 | 2/2009 | Kahn et al. |
| 2009/0063099 A1 | 3/2009 | Counts et al. |
| 2009/0240461 A1* | 9/2009 | Makino .............. A61B 5/1123 702/141 |
| 2009/0319221 A1 | 12/2009 | Kahn et al. |
| 2010/0030350 A1 | 2/2010 | House et al. |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony, III et al. |
| 2010/0217099 A1 | 8/2010 | Leboeuf et al. |
| 2010/0274102 A1 | 10/2010 | Teixeira |
| 2010/0298656 A1 | 11/2010 | McCombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0006112 A1* | 1/2012 | Lee .................. G06F 3/0346 73/504.02 |
| 2012/0083715 A1 | 4/2012 | Friedman |
| 2012/0172677 A1 | 7/2012 | Beith |
| 2012/0238832 A1 | 9/2012 | Hwang |
| 2012/0296455 A1 | 11/2012 | Ohnemus et al. |
| 2012/0322621 A1 | 12/2012 | Bingham et al. |
| 2013/0023739 A1 | 1/2013 | Russel |
| 2013/0041590 A1 | 2/2013 | Burich et al. |
| 2013/0053990 A1 | 2/2013 | Ackland |
| 2013/0085861 A1 | 4/2013 | Dunlap |
| 2013/0096943 A1 | 4/2013 | Carey et al. |
| 2013/0135097 A1 | 5/2013 | Doezema |
| 2013/0158686 A1 | 6/2013 | Zhang et al. |
| 2013/0178335 A1 | 7/2013 | Lin et al. |
| 2013/0197377 A1 | 8/2013 | Takahiko et al. |
| 2013/0218053 A1 | 8/2013 | Kaiser et al. |
| 2013/0267794 A1 | 10/2013 | Fernstrom et al. |
| 2014/0071082 A1 | 3/2014 | Singh et al. |
| 2014/0073486 A1 | 3/2014 | Ahmed et al. |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0121471 A1 | 5/2014 | Walker |
| 2014/0167973 A1 | 6/2014 | Letchner et al. |
| 2014/0172238 A1 | 6/2014 | Craine |
| 2014/0172361 A1* | 6/2014 | Chiang ............. G01C 22/006 702/160 |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1 | 7/2014 | Lee et al. |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266789 A1 | 9/2014 | Matus |
| 2014/0276127 A1 | 9/2014 | Ferdosi et al. |
| 2014/0278139 A1* | 9/2014 | Hong ................ A61B 5/4866 702/19 |
| 2014/0278229 A1 | 9/2014 | Hong et al. |
| 2014/0316305 A1 | 10/2014 | Venkatraman et al. |
| 2014/0348367 A1 | 11/2014 | Vavrus et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0105096 A1 | 4/2015 | Chowdhury et al. |
| 2015/0119728 A1 | 4/2015 | Blackadar et al. |
| 2015/0147734 A1 | 5/2015 | Flores et al. |
| 2015/0148632 A1 | 5/2015 | Benaron |
| 2015/0182149 A1 | 7/2015 | Rapoport et al. |
| 2015/0250417 A1 | 9/2015 | Cheng et al. |
| 2015/0256689 A1 | 9/2015 | Erkkila et al. |
| 2015/0260514 A1 | 9/2015 | Menelas et al. |

(56) References Cited

U.S. PATENT DOCUMENTS

| | | |
|---|---|---|
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0357948 A1 | 12/2015 | Goldstein |
| 2015/0374240 A1 | 12/2015 | Lee |
| 2016/0021238 A1 | 1/2016 | Abramson et al. |
| 2016/0054449 A1 | 2/2016 | Pekonen et al. |
| 2016/0057372 A1 | 3/2016 | Raghuram et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0084869 A1 | 3/2016 | Yuen et al. |
| 2016/0147319 A1 | 5/2016 | Agarwal et al. |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0242646 A1 | 8/2016 | Obma |
| 2016/0256058 A1 | 9/2016 | Pham et al. |
| 2016/0269572 A1 | 9/2016 | Erkkila et al. |
| 2016/0287177 A1 | 10/2016 | Huppert et al. |
| 2016/0314633 A1 | 10/2016 | Bonanni et al. |
| 2016/0361020 A1 | 12/2016 | LeBoeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roover et al. |
| 2017/0061817 A1 | 3/2017 | Mettler May |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0181644 A1 | 6/2017 | Meer et al. |
| 2017/0188893 A1 | 7/2017 | Venkatraman et al. |
| 2017/0202486 A1 | 7/2017 | Martikka et al. |
| 2017/0211936 A1 | 7/2017 | Howell et al. |
| 2017/0242499 A1 | 8/2017 | Shah et al. |
| 2017/0242500 A1 | 8/2017 | Shah et al. |
| 2017/0251972 A1 | 9/2017 | Jayaraman et al. |
| 2017/0259116 A1 | 9/2017 | Mestas |
| 2017/0269734 A1 | 9/2017 | Graff |
| 2017/0269785 A1 | 9/2017 | Abdollahian et al. |
| 2017/0273619 A1 | 9/2017 | Alvarado et al. |
| 2017/0347885 A1 | 12/2017 | Tan et al. |
| 2017/0367658 A1 | 12/2017 | LeBoeuf et al. |
| 2018/0028863 A1 | 2/2018 | Matsuda |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |
| 2018/0056129 A1 | 3/2018 | Narasimha Rao et al. |
| 2018/0279914 A1 | 10/2018 | Patek et al. |
| 2019/0076063 A1 | 3/2019 | Kent et al. |

FOREIGN PATENT DOCUMENTS

| | | |
|---|---|---|
| CN | 104218976 A | 12/2014 |
| CN | 105031905 A | 11/2015 |
| CN | 105068656 A | 11/2015 |
| GB | 2465824 | 6/2010 |
| IN | 259/KOL/2015 | 12/2015 |
| JP | 2010-051333 A | 3/2010 |
| JP | 2013-039316 A | 2/2013 |
| JP | 2014-042757 A | 3/2014 |
| JP | 2016-150018 A | 8/2016 |
| JP | 2018-000543 A | 1/2018 |
| JP | 2018-015187 A | 2/2018 |
| RO | 122807 B1 | 2/2010 |
| WO | 03/61779 A1 | 7/2003 |
| WO | 2010090867 | 8/2010 |
| WO | 2011/105914 A1 | 9/2011 |
| WO | 2015/126182 A1 | 8/2015 |
| WO | 2015/200900 A1 | 12/2015 |
| WO | 2016/044831 A1 | 3/2016 |
| WO | 2016/073620 A1 | 5/2016 |

OTHER PUBLICATIONS

KINprof, May 31, 2011, Predictive VO2max tests, Web Video, Retrieved from: https://www.youtube.com/watch?v=_9e3HcY1sm8.

PCT International Application No. PCT/US2017/049693, International Search Report dated Aug. 12, 2017, 3 pages.

Novatel, "IMU Error and Their Effects", Novatel Application Notes APN-064 Rev A p. 1-6, Feb. 21, 2014.

Le, et al., "Sensor-based Training Optimization of a Cyclist Group", Seventh International Conference on Hybrid Intelligent Systems, IEEE 2007, pp. 265-270.

Yamaji, et al., "Relationship Between Heart Rate and Relative Oxygen Intake in Male Subjects Aged 10 to 27 Years", J. Human Ergol., 7:29-39, Jan. 27, 1978.

Your Fitness FAQ, Why is it important to warm up and cool down in a workout?, 2012, Web, Retrieved from: http://www.yourfitnessfaq.com/whyisitimportanttowarmupandcooldowninaworkout.html.

Vella et al, Exercise After-Burn: Research Update, 2005, Web, Retrieved from: http://www.unm.edu/~lkravitz/Article%20folder/epocarticle.html.

Song et al., "Training Activity Recognition Systems Online Using Real-Time Crowdsourcing", University of Rochester Computer Science, UbiCom' 12, Sep. 5-8, 2012 (2 pages).

Rowlands et al., "Assessing Sedentary Behavior with the GENEActiv: Introducing the Sedentary Sphere". Medicine and science in sports and exercise 46.6 (2014): 1235-1247.

Hasson et al., "Accuracy of four resting metabolic rate production equations: Effects of sex, body mass index, age, and race/ethnicity", Journal of Science and Medicine in Sport, 2011, vol. 14, p. 344-351.

Lucas et al., "Mechanisms of orthostatic intolerance following very prolonged exercise", 2008, J Appl Physiol, 105: 213-225.

Kunze et al., "Where am i: Recognizing on-body positions of wearable sensors." Location- and context-awareness. Springer Berlin Heidelberg, 2005. 264-275.

Keytel et al., "Prediction of energy expenditure from heart rate monitoring during submaximal exercise", 2005, Journal of Sports Sciences, 23(3):289-97.

Sabatini, Kalman-filter-based orientation determination using inertial/magnetic sensors: observability analysis and performance evaluation, Sep. 27, 2011, Sensors 2011, 11, 9182-9206.

Jackson et al., "Prediction of functional aerobic capacity without exercise testing", Medicine and Science in Sports and Exercise, 22(6), 863-870, 1990.

Isaacs et al., "Modeling energy expenditure and oxygen consumption in human exposure models: accounting for fatigue and EPOC", 2008, Journal of Exposure Science and Environmental Epidemiology, 18: 289-298.

Human Kinetics, Aerobic Workout Components, 2011, Web, Retrieved from: http://www.humankinetics.com/excerpts/excerpts/aerobicworkoutcomponentsexcerpt.

Gao et al., "Evaluation of accelerometer based multi-sensor versus single-sensor activity recognition systems." Medical engineering & physics 36.6 (2014): 779-785.

Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.

Chu, "In-Vehicle Driver Detection Using Mobile Phone Sensors", Submitted for Graduation with departmental Distinction in Electrical and Computer Engineering, Apr. 20, 2011, pp. 1-21.

Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.

(56) References Cited

OTHER PUBLICATIONS

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).
Noakes, Timothy D., "Lore of Running," Fourth Edition, Human Kinetics, Chapter 2: Oxygen Transport and Running Economy, Chapter 3: Energy Systems and Running Performance, 157 pages (2002).
Rapoport, Benjamin I., "Metabolic Factors Limiting Performance in Marathon Runners," PLoS Computational Biology, vol. 6, Issue 10, 13 pages (Oct. 2010).
Tanaka, H. et al., "Age-predicted maximal heart rate revisited," Journal of the American College of Cardiology, vol. 37, Issue 1, pp. 153-156 (Jan. 2001).
Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).
Kyle, Chester R., "Reduction of Wind Resistance and Power Output of Racing Cyclists and Runners Travelling in Groups", Ergonomics, vol. 22, No. 4, 1979, pp. 387-397.
U.S. Appl. No. 17/015,912, filed Sep. 9, 2020, Humblet et al.
U.S. Appl. No. 17/015,965, filed Sep. 9, 2020, Dervisoglu et al.
U.S. Appl. No. 17/016,020, filed Sep. 9, 2020, Ochs et al.
Alexander, "Energetics and Optimization of Human Walking and Running," Am J Human Biology, Mar. 20, 2002, 14:641-648.
Lasecki, "Real-Time Crowd Labeling for Deployable Activity Recognition," University of Rochester Computer Science, Feb. 23, 2013, 10 pages.
Latt et al., "Walking speed, cadence and step length are selected to optimize the stability of head and pelvis accelerations," Experimental Brain Research, Aug. 24, 2007, 184: 201-209.
Morgan et al., "Effect of step length optimization on the aerobic demand of running," Journal of Applied Physiology, 1994, 245-251.
PCT International Preliminary Report on Patentability in International Appln. No. PCT/US2017/049693, dated Mar. 5, 2019, 8 pages.
PCT International Preliminary Report on Patentability in International Appln. No. PCT/US2018/047290, dated Mar. 17, 2020, 9 pages.
Pfitzinger.com "Optimal Marathon Training Sessions, Distance Coach. com, Intelligent Training for Distance Runners," archived May 15, 2012, <https://web.archive.org/web/20120515081237/http://www.pfitzinger.com/marathontraining.shtml>, printed Jan. 20, 2017, 3 pages.
Romijn et al., "Regulation of endogenous fat and carbohydrate metabolism in relation to exercise intensity and duration," Am. J. Physiol., 1993, 6:1-13.
Triendurance.com "Running with a Higher Cadence, Triendurance," Oct. 23, 2021, retrieved from <https://web.archive.org/web/20080228162904/http://www.trienduranee.com/Related.asp?PageID=14&NavID=7>, 2 pages.
Bruce, R.A. et al., "Exercising testing in adult normal subjects and cardiac patients," Pediatrics, vol. 32, No. Suppl., pp. 742-756 (Oct. 1963).
Bruce, R.A. et al., "Maximal oxygen intake and nomographic assessment of functional aerobic impairment in cardiovascular disease," American Heart Journal, vol. 85, Issue 4, pp. 546-562 (Apr. 1973).
Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).
Cavanagh, P.R. et al., "The effect of stride length variation on oxygen uptake during distance running," Medicine and Science in Sports and Exercise, vol. 14, No. 1, pp. 30-35 (1982).
Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).
Fox, S.M. et al., "Physical Activity and the Prevention of Coronary Heart Disease," Bull. N.Y. Acad. Med., vol. 44, No. 8, pp. 950-967 (Aug. 1968).
Glass, S., et al., "ACSM's Metabolic Calculations Handbook," Lippincott Williams & Wilkins, 124 pages (2007).
Lavie, C.J. et al., "Impact of cardiorespiratory fitness on the obesity paradox in patients with heart failure," Mayo Clinic Proceedings, vol. 88, No. 3, pp. 251-258 (Mar. 2013).
Margaria, R. et al., "Energy cost of running," Journal of Applied Physiology, vol. 18, No. 2, pp. 367-370 (Mar. 1, 1963).
Myers, J. et al., "Exercise Capacity and Mortality Among Men Referred for Exercise Testing," The New England Journal of Medicine, vol. 346, No. 11, pp. 793-801 (Mar. 14, 2002).

\* cited by examiner

FITNESS TRACKING FOR CONSTRAINED-ARM USAGE

FIELD

The present disclosure relates generally to fitness tracking devices and, more particularly, to wearable devices used in conjunction with human activities in which a user's arm may be constrained, such as pushing a stroller.

BACKGROUND

Fitness tracking devices may detect user motion using one or more sensors, such as accelerometers, gyroscopes, barometers, and GPS (Global Positioning Satellite) receivers. Using motion data obtained from these sensors, a fitness tracking device may calculate and output various fitness data of interest to the user, such as number of steps taken, distance traveled, speed, caloric expenditure, and exercise time.

Smartwatches and other arm-worn devices may sense arm swing motion to determine the user's stride length. For example, fitness tracking devices may use accelerometer energy to calculate stride length. Stride length, along with step cadence, may be used to determine the user's speed among other fitness data. If the user's arm motion is constrained, some fitness tracking devices may underestimate stride length, leading to inaccurate fitness data being presented to the user.

Some fitness tracking devices may estimate the amount of work being performed based on the user's body mass and speed. Even if the user's stride length could be accurately determined when the arm is constrained, the calculated fitness data may not account for the increased work performed when pushing a stroller or other substantial load.

SUMMARY

According to one aspect of the present disclosure, method comprises: collecting motion data using a fitness tracking device located on an arm of a user; detecting, by a processor circuit, that the arm is constrained based on the motion data; estimating, by a processor circuit, a stride length of the user based on the motion data and historical step cadence-to-stride length data; calculating, by a processor circuit, fitness data using the estimated stride length; and outputting the fitness data to the user.

In some embodiments, calculating the fitness data comprises calculating at least one of distance traveled, speed, caloric expenditure, or exercise time. In certain embodiments, detecting that the arm is constrained comprises: determining a pose angle based on the motion data; determining an accelerometer energy based on the motion data; and detecting that the arm is constrained based on the pose angle and the accelerometer energy. In particular embodiments, detecting that the arm is constrained based on the pose angle comprises detecting that the arm is constrained if the pose angle is within a predetermined range of pose angles. In some embodiments, the predetermined range of pose angles corresponds to pose angles greater than about −45°.

In certain embodiments, estimating the stride length of the user based on historical step cadence-to-stride length data comprises: obtaining a plurality of step cadence-to-stride length pairs; interpolating the plurality of step cadence-to-stride length pairs to generate a curve; and finding a point on the curve corresponding to a measured step cadence of the user. In some embodiments, obtaining the plurality of step cadence-to-stride length pairs comprises obtaining calibration data for the user. In particular embodiments, obtaining the plurality of step cadence-to-stride length pairs comprises obtaining data for a general population of users.

In some embodiments, the method comprises: detecting, by a processor circuit, that the user is pushing an object across a surface based on the motion data; and estimating an increased load due to the object being pushed, wherein calculating the fitness data comprises calculating the fitness data based on the estimated increased load. In certain embodiments, detecting that the user is pushing an object across a surface comprises: calculating, by a processor circuit, road noise as a ratio of accelerometer data within a first frequency band to accelerometer energy within a second frequency band; and comparing, by a processor circuit, the road noise to a threshold value. In some embodiments, the first frequency band comprises frequencies above 20 Hz and the second frequency band comprises frequencies below 4 Hz.

According to another aspect of the present disclosure, a system comprises: a motion sensor located on an appendage of a user and configured to collect motion data; and a processor circuit coupled to the motion sensor and configured to execute instructions causing the processor circuit to perform embodiments of the method described above.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Embodiments of the present disclosure may improve the accuracy of fitness tracking in situations where a user's arm is constrained due to, for example, the user pushing a stroller, holding a beverage or a phone while walking, holding handrails on a treadmill, etc. A constrained-arm condition may be detected by analyzing motion data and, in response, the user's stride length may be estimated using historical step cadence-to-stride length data. The estimated stride length may be used to improve the accuracy of fitness data, such as distance traveled, speed, caloric expenditure, and exercise time. In some embodiments, the accuracy of fitness data may be further improved by accounting for increased load due to the user pushing a stroller or other object across a surface. Motion data may be used to detect that the user is pushing an object and, in response, increased load due to the object may be inferred and used to improve the accuracy of fitness data.

Figure 1:
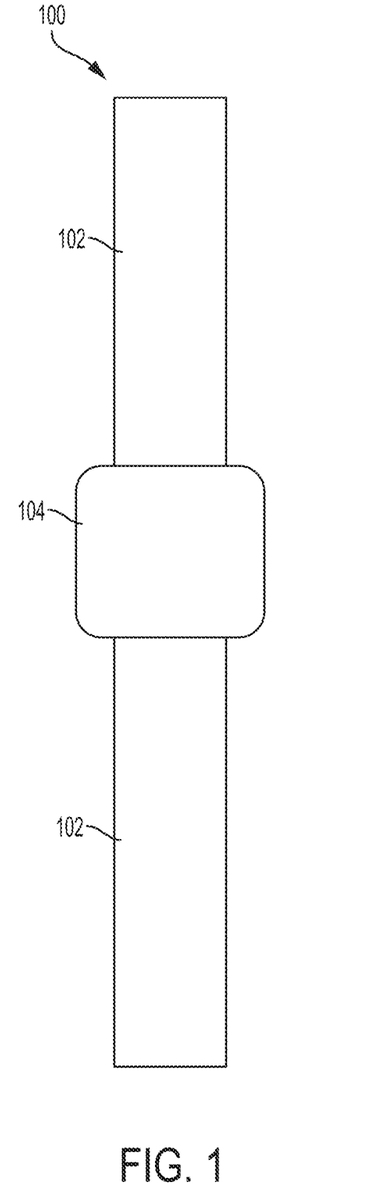
FIG. 1 shows an example of a fitness tracking device, according to some embodiments of the present disclosure.

FIG. 1 shows an example of a fitness tracking device 100, according to some embodiments of the present disclosure. The illustrative fitness tracking device 100 includes band 102 and housing 104. The band 102 may be used to attach the fitness tracking device 100 to a user's arm. The housing 104 may include one or more components described below in conjunction with FIG. 2. In certain embodiments, the fitness tracking device 100 is designed to be worn on the user's wrist.

Figure 2:
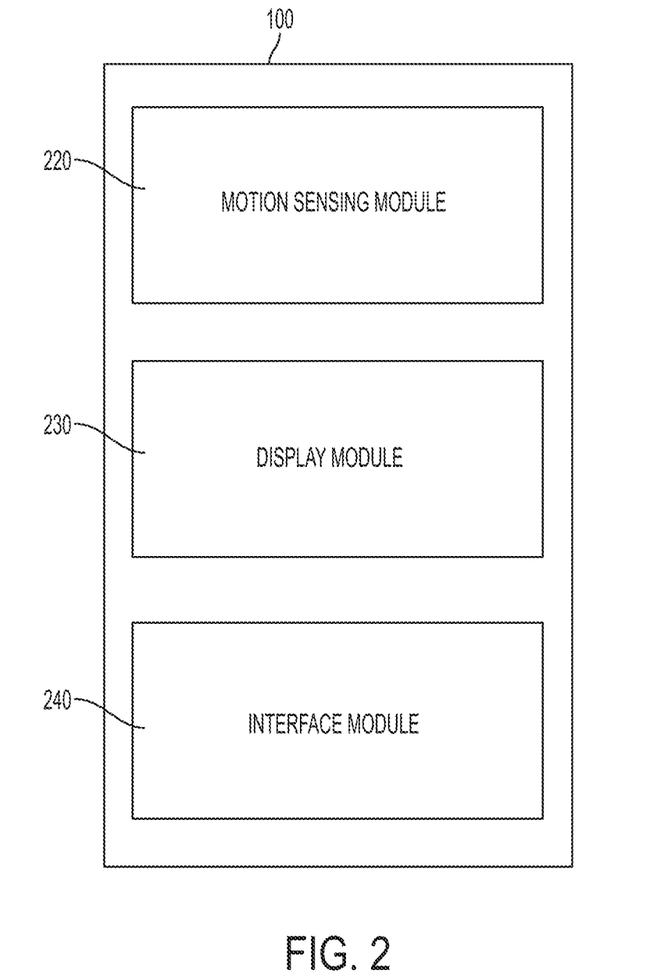
FIG. 2 depicts a block diagram of illustrative components that may be found within a fitness tracking device, according to some embodiments of the present disclosure.

FIG. 2 depicts a block diagram of example components that may be found within a fitness tracking device (e.g., fitness tracking device 100 of FIG. 1), according to some embodiments of the present disclosure. These components may include a motion sensing module 220, a display module 230, and an interface module 240.

The motion sensing module 220 may include one or more motion sensors, such as an accelerometer or a gyroscope. In some embodiments, the accelerometer may be a three-axis, microelectromechanical system (MEMS) accelerometer, and the gyroscope may be a three-axis MEMS gyroscope. A microprocessor (not shown) or motion coprocessor (not shown) of the fitness tracking device 100 may receive data from the motion sensors of the motion sensing module 220 to track acceleration, rotation, position, or orientation information of the fitness tracking device 100 in six degrees of freedom through three-dimensional space.

In some embodiments, the motion sensing module 220 may include other types of sensors in addition to accelerometers and gyroscopes. For example, the motion sensing module 220 may include an altimeter or barometer, or other types of location sensors, such as a GPS sensor. A barometer (also referred to herein as a barometric sensor) can detect pressure changes and correlate the detected pressure changes to an altitude.

Display module 230 may be a screen, such as a crystalline (e.g., sapphire) or glass touchscreen, configured to provide output to the user as well as receive input form the user via touch. For example, display module 230 may be configured to display the number of steps the user has taken, distance traveled, speed, caloric expenditure, exercise time, amount other fitness data. Display module 230 may receive input from the user to select, for example, which information should be displayed, or whether the user is beginning a physical activity (e.g., starting a session) or ending a physical activity (e.g., ending a session), such as a running session or a cycling session. In some embodiments, the fitness tracking device 100 may present output to the user in other ways, such as by producing sound with a speaker (not shown), and the fitness tracking device 100 may receive input from the user in other ways, such as by receiving voice commands via a microphone (not shown).

In some embodiments, the fitness tracking device 100 may communicate with external devices via interface module 240, including a configuration to present output to a user or receive input from a user. Interface module 240 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as LTE or a Wi-Fi (IEEE 802.11) protocol. In other embodiments, interface module 240 may include wired interfaces, such as a headphone jack or bus connector (e.g., Lightning, Thunderbolt, USB, etc.).

In certain embodiments, the fitness tracking device 100 may be configured to communicate with a companion device, such as companion device 300 shown in FIG. 3 and described below in conjunction therewith. In some embodiments, the fitness tracking device 100 may be configured to communicate with other external devices, such as a notebook or desktop computer, tablet, headphones, Bluetooth headset, etc.

The modules described above are examples, and embodiments of the fitness tracking device 100 may include other modules not shown. For example, fitness tracking device 100 may include one or more microprocessors (not shown) for processing sensor data, motion data, other information in the fitness tracking device 100, or executing instructions for firmware or apps stored in a non-transitory processor-readable medium such as a memory module (not shown). Additionally, some embodiments of the fitness tracking device 100 may include a rechargeable battery (e.g., a lithium-ion battery), a microphone or a microphone array, one or more cameras, one or more speakers, a watchband, a crystalline (e.g., sapphire) or glass-covered scratch-resistant display, water-resistant casing or coating, etc.

Figure 3:
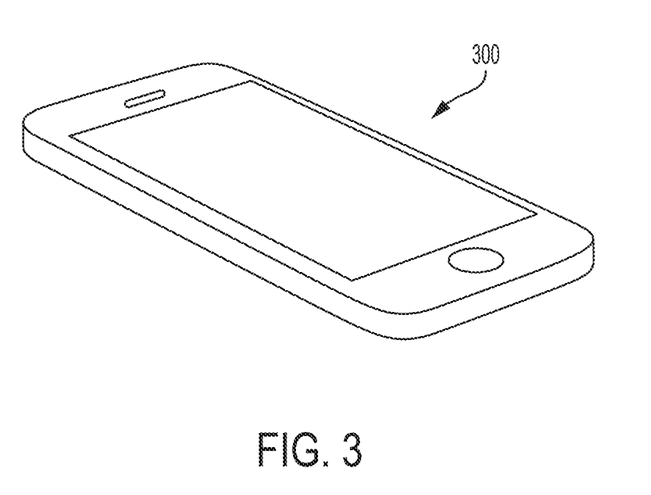
FIG. 3 shows an example of a companion device, according to some embodiments of the present disclosure.

FIG. 3 shows an example of a companion device 300, according to some embodiments of the present disclosure. The fitness tracking device 100 may be configured to communicate with the companion device 300 via a wired or wireless communication channel (e.g., Bluetooth, Wi-Fi, etc.). In some embodiments, the companion device 300 may be a smartphone, tablet, or similar portable computing device. The companion device 300 may be carried by the user, stored in the user's pocket, strapped to the user's arm with an armband or similar device, placed on a table, or otherwise positioned within communicable range of the fitness tracking device 100.

The companion device 300 may include a variety of sensors, such as location and motion sensors (not shown). When the companion device 300 may be optionally available for communication with the fitness tracking device 100, the fitness tracking device 100 may receive additional data from the companion device 300 to improve or supplement its calibration or calorimetry processes. For example, in some embodiments, the fitness tracking device 100 may not include a GPS sensor as opposed to an alternative embodiment in which the fitness tracking device 100 may include a GPS sensor. In the case where the fitness tracking device 100 may not include a GPS sensor, a GPS sensor of the companion device 300 may collect GPS location information, and the fitness tracking device 100 may receive the GPS location information via interface module 240 (FIG. 2) from the companion device 300.

In another example, the fitness tracking device 100 may not include an altimeter, as opposed to an alternative embodiment in which the fitness tracking device 100 may include an altimeter. In the case where the fitness tracking device 100 may not include an altimeter or barometer, an altimeter or barometer of the companion device 300 may collect altitude or relative altitude information, and the fitness tracking device 100 may receive the altitude or relative altitude information via interface module 240 (FIG. 2) from the companion device 300.

In various embodiments, fitness tracking device 100 may use motion data, such as accelerometer or gyroscope data, to determine if a user is engaging in a constrained-arm activity and/or if the user is pushing an object across a surface. In certain embodiments, fitness tracking device 100 may calculate one or more features of interest from motion data and use such features to detect the aforementioned usages. Non-limiting examples of features that may be used include pose angle, accelerometer energy, and step cadence.

As used herein, "pose angle" refers to an angle of the user's arm with respect to the horizon. In some embodiments, pose angle may be estimated using techniques disclosed in U.S. Pat. No. 9,526,430, entitled "Method and System to Estimate Day-Long Calorie Expenditure Based on Posture," which his hereby incorporated by reference in its entirety. In some embodiments, the fitness tracking device 100 may be embodied as a smartwatch, and pose angle may be determined as an angle between the watch's crown and the horizon.

Accelerometer energy (or "signal energy") may be measured using a norm-2 metric. The energy calculation can occur in either time or frequency domains. In the time domain, accelerometer energy can be calculated as the variance over a window of accelerometer samples over one or more axes. In the frequency domain, accelerometer energy can be calculated by selecting a certain frequency range to calculate the accelerometer signal energy, particularly by summing the squared value of the frequency bins of an FFT for one or more axes.

The user's step cadence may be obtained from a motion sensor or otherwise calculated from motion sensor data. In some embodiments, step cadence may be determined using techniques disclosed in U.S. Pat. App. Pub. No. 2015/0088006, entitled "Method for determining aerobic capacity," which his hereby incorporated by reference in its entirety.

Figure 4:
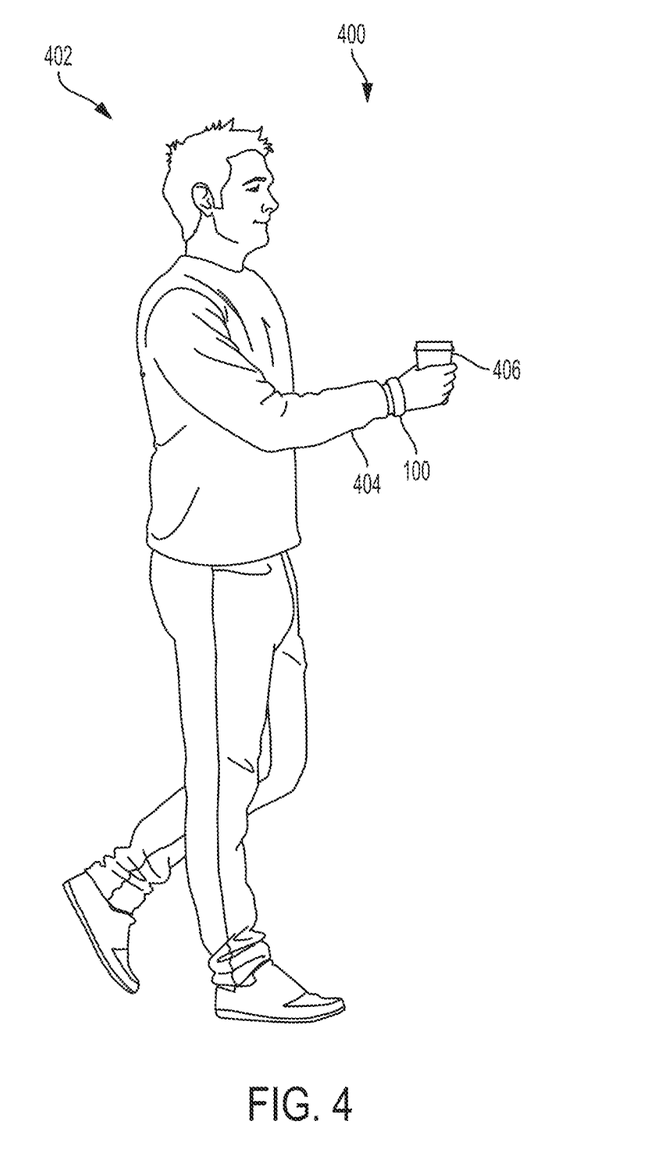
FIG. 4 illustrates a fitness tracking device used with a constrained arm, according to some embodiments of the present disclosure.

FIG. 4 is a diagram 400 showing a fitness tracking device 100 being used with a constrained arm. In this example, user 402 is carrying an object 406 (e.g., a beverage) with an arm 404, and has a fitness tracking device 100 attached to the same arm 404. While ambulatory, the user 402 may purposefully constrain movement of arm 404 to prevent the object 406 from tipping or otherwise being displaced.

Figure 5:
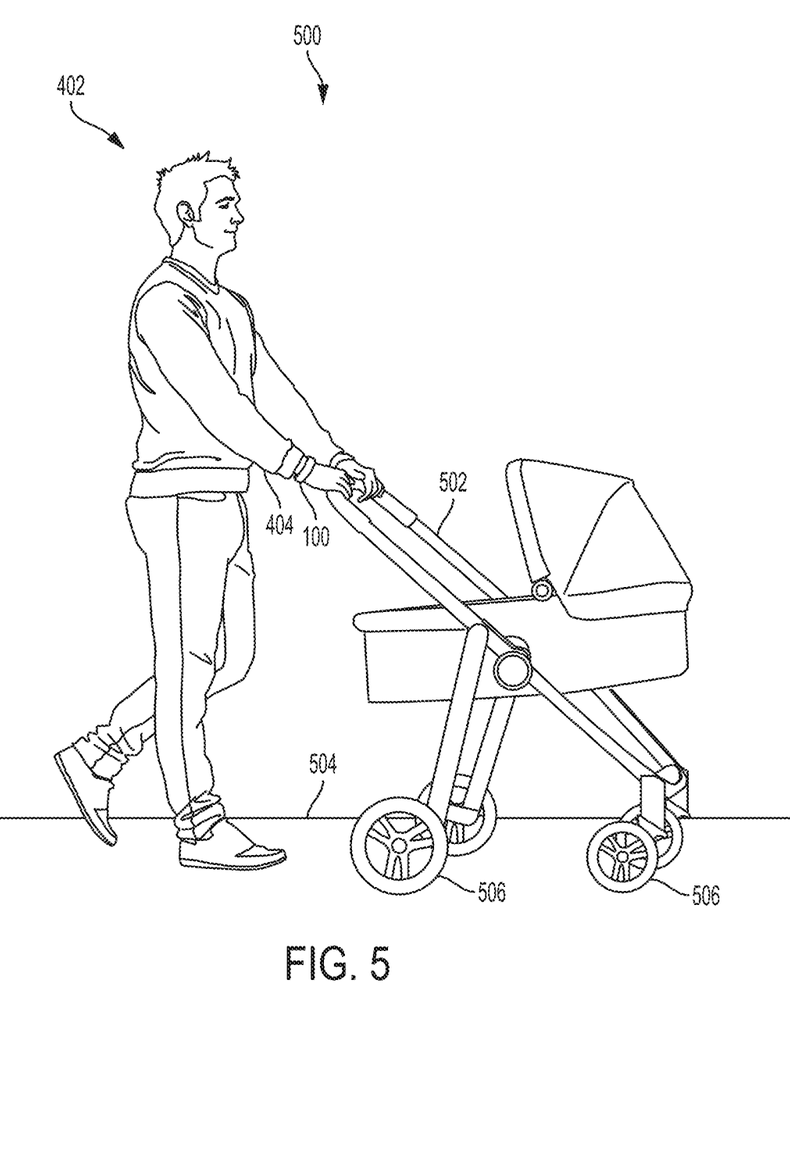
FIG. 5 illustrates a fitness tracking device used while pushing an object across a surface, according to some embodiments of the present disclosure.

FIG. 5 is a diagram 500 illustrating another constrained-arm scenario. User 402 may wear a fitness tracking device 100 on the same arm 404 used to push an object 502 across a surface 502. In the example of FIG. 5, the object is shown as a stroller 502, however the present disclosure is applicable to other types of objects that may be pushed across a surface, such as a shopping carriage, a walker, etc. As the user pushes the object 502, the interaction between the object 502 and the surface 504 may produce vibrations or other disturbances that are detected as relatively high-frequency accelerometer energy by the fitness tracking device 100. In the case of a stroller or other wheeled object 502, the high-frequency energy may result from an interaction between wheels 506 (and/or a suspension system coupled thereto) and the surface 504. The accelerometer may detect both high-frequency energy from the object being pushed, and relatively low-frequency energy ("pedestrian band energy") from the user's motion. In certain embodiments, accelerometer energy from the object being pushed has frequency greater than 20 Hz and accelerometer energy from user's motion may have a frequency less than 4 Hz.

Figure 6:
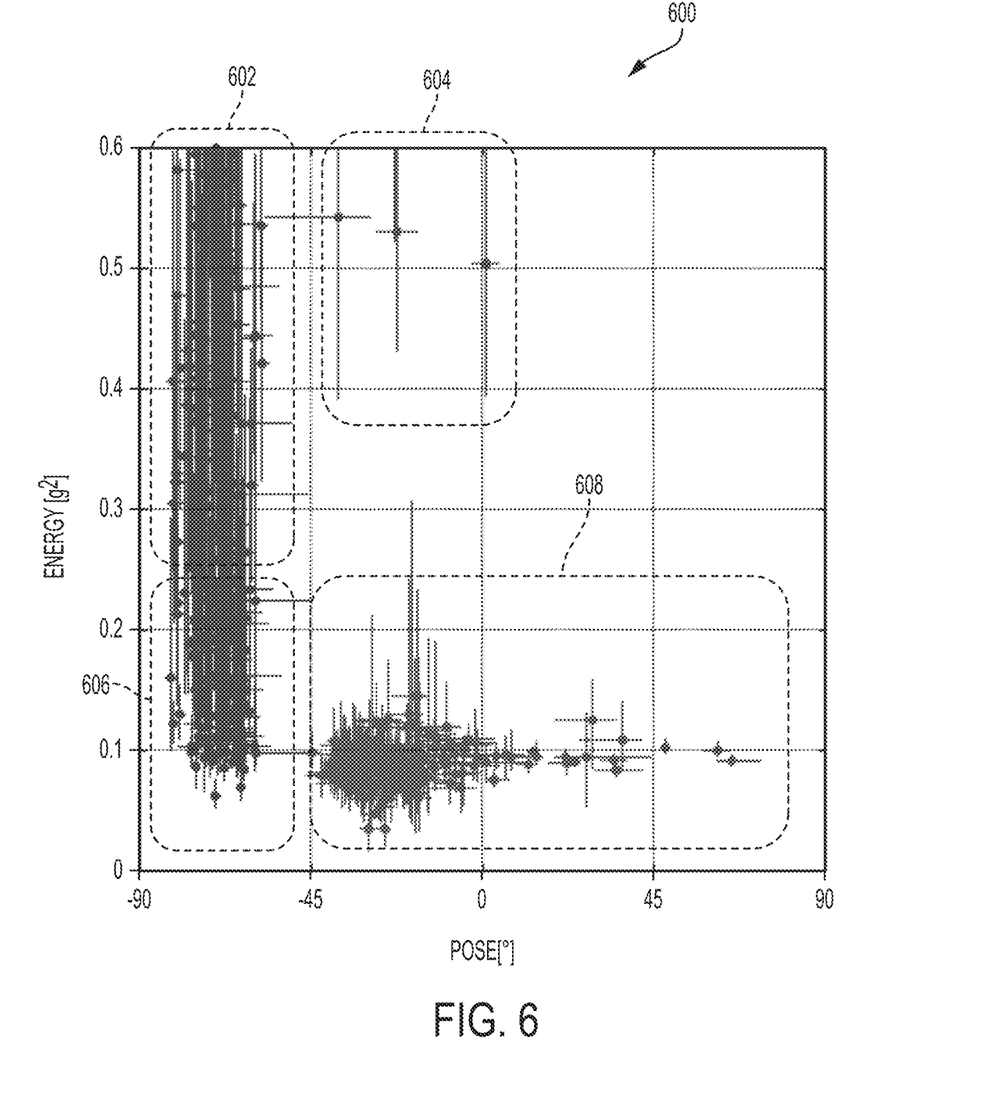
FIG. 6 is a graph of pose angle versus accelerometer energy, according to embodiments of the present disclosure.

Referring to FIG. 6, a graph 600 illustrates pose angle (shown along the horizontal axis) and accelerometer energy (shown along the vertical axis) for different scenarios in which a user is wearing a fitness tracking device on an arm. Pose angle may be defined as the angle between the forearm and the horizon, and may be computed in real-time using accelerometer data as described in U.S. Pat. No. 9,526,430, entitled "Method and System to Estimate Day-Long Calorie Expenditure Based on Posture." If the arm is not constrained, pose angle may tend to be in the range −90° to −45° as the user walks, jogs, or runs. However, if the user's arm is constrained (e.g., as a result of holding or pushing an object), pose angle may tend to be in the range −45° to +45°.

Within the illustrative graph 600, region 602 may correspond to a scenario where the user is walking at a normal speed with the arm unconstrained; region 604 to a scenario where the user is walking at a relatively fast speed (e.g., speed walking) with the arm unconstrained; region 606 to a scenario where the user is walking at a relatively slow speed with the arm unconstrained; and region 608 to a scenario where the user's arm is constrained. As can be seen in the figure, using pose angle on its own may be insufficient to differentiate between speed walkers 604 and constrained-arm usage 608. Likewise, using accelerometer energy on its own may be insufficient to differentiate between slow walkers 606 and a constrained-arm usage 608. Accordingly, some embodiments of the present disclosure use at least two different features (e.g., pose angle and accelerometer energy) to detect that the arm onto which the fitness tracking device is attached is constrained. In particular embodiments, constrained-arm usage may be detected if pose angle is greater than about −45° and accelerometer energy is less than about 0.25 $g^2$.

Typically, a fitness tracking device may use accelerometer energy to estimate the user's stride length. However, if the user's arm is constrained, accelerometer energy may decrease (as illustrated by region 608), which in turn may result in the stride length being underestimated. Thus, in some embodiments, when a constrained-arm condition is detected, stride length may be estimated using historical step cadence-to-stride length data.

Figure 7:
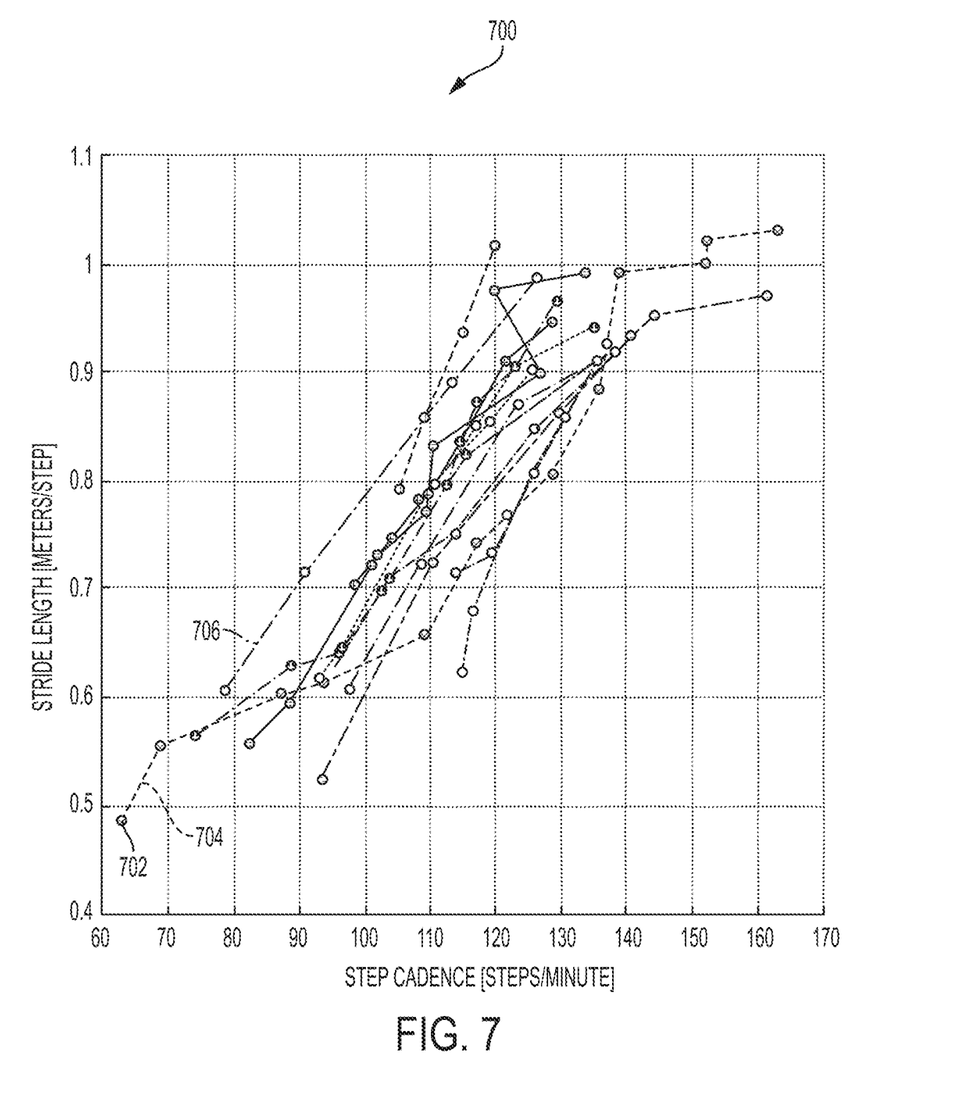
FIG. 7 is a graph of step cadence versus stride length, according to some embodiments of the present disclosure.

FIG. 7 shows a graph 700 illustrating historical step cadence-to-stride length data. According to biomechanics, step cadence and stride length are related. Each point in the graph 700 may correspond to a step cadence-to stride length pair that was previously measured or otherwise collected for a user. For example, point 702 may indicate that, during some time epoch, a user averaged 63 steps per minute with an average stride length of about 0.48 meters. Multiple pairs collected for the same user may be plotted and interpolated to generate a curve. For example, as shown in FIG. 7, a first curve 704 may correspond to stride data measured for a first user, and a second curve 706 may correspond to stride data measured for a second user. The user's stride length can be estimated by finding a point on the historical data curve corresponding to a currently measured step cadence.

Step cadence and stride length data may be collected by, and stored within, the user's own fitness tracking device as part of a calibration process. If a constrained-arm is subsequently detected, the stored calibration data may be used to estimate stride length based on currently measured step cadence. If such calibration data is not available, historical step cadence-to-stride length data from a general population of users may be used instead. Such general population data may be configured within the fitness tracking device and/or a companion device. Estimating stride length using historical step cadence-length data may allow the fitness tracking device to provide accurate fitness data (e.g., distance, speed, caloric expenditure, and exercise time) even during constrained-arm usage.

Figure 8:
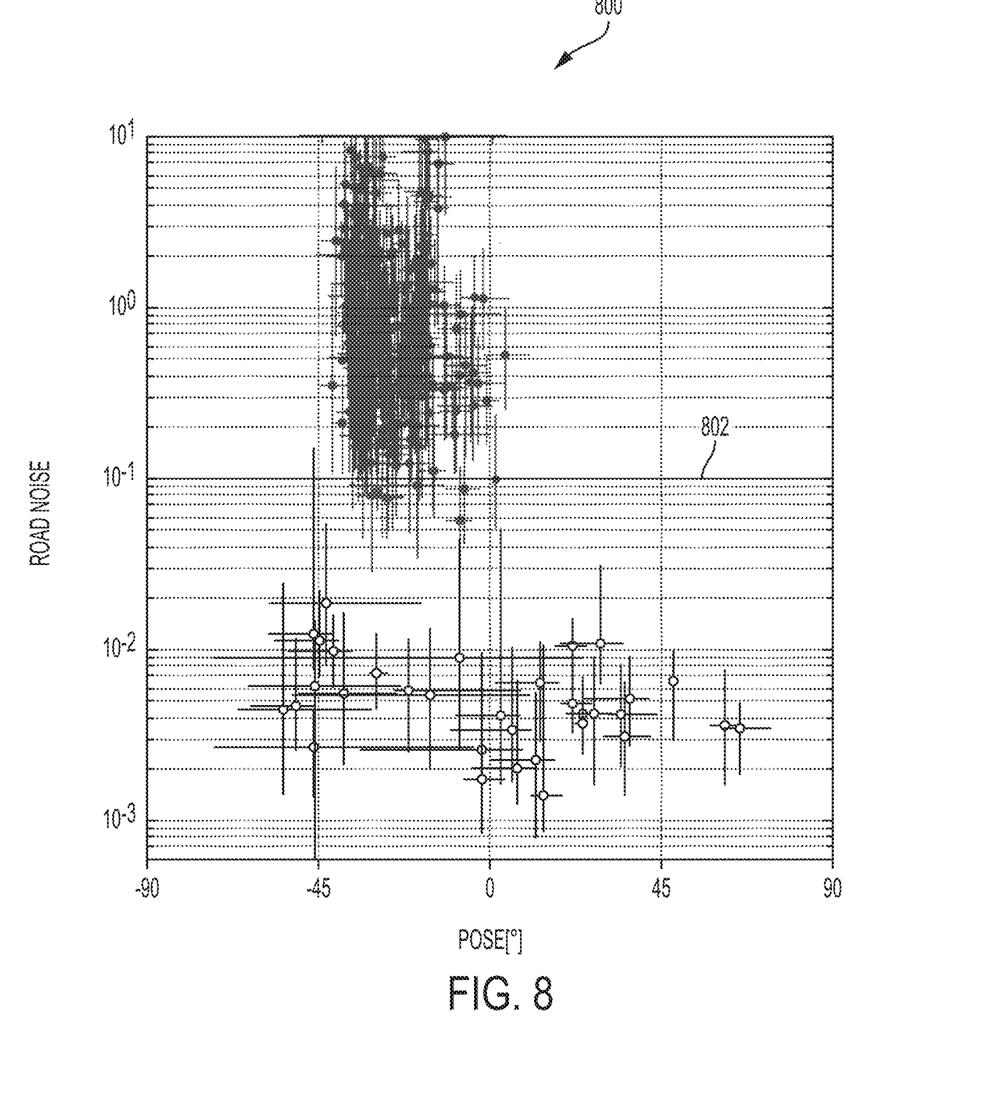
FIG. 8 is a graph of pose angle versus road noise, according to embodiments of the present disclosure.

Referring to FIG. 8, according to an embodiment of the present disclosure, a "road noise" feature may be used detect when the user is pushing an object (e.g., a stroller) across a surface. Road noise may be defined as the ratio of high-frequency energy to low-frequency energy experienced by an accelerometer, where "low" frequency may correspond to a bandwidth of energy produced during typical pedestrian motion, and "high" frequency may correspond to a bandwidth above the pedestrian band. In some embodiments, high-frequency energy is defined as energy having a frequency greater than 20 Hz, and low-frequency energy is defined as energy having a frequency below 4 Hz.

FIG. 8 shows a graph 800 illustrating pose angle (horizontal axis) versus road noise (vertical axis) for two scenarios in which the user has a fitness tracking device attached to an arm. Data points generally below line 802 may correspond to a scenario where a user's arm is constrained but not being used to push an object, whereas data points generally above line 802 may correspond to a scenario where the user is pushing a stroller or other object across a surface using the arm. As can be seen in the example of FIG. 8, in the case where the user's arm is pushing an object, the amount of road noise may be increased and more concentrated (in terms of pose angle) relative to when the arm is not pushing an object. Accordingly, in some embodiments, it may be detected that the user is pushing an object when road noise is above a predetermined threshold (e.g., $10^{-1}$). In certain embodiments, only road noise within a certain range of pose angles (e.g., −45° to 0°) is considered when detecting if the user is pushing an object across a surface.

In response to detecting that the user is pushing an object, an increased load may be estimated and used to calculate more accurate fitness data (e.g., more accurate caloric expenditure and/or exercise time information). In one embodiment, the increased load may be estimated based on the weight and mechanics of a typical stroller. The increased load may be determined experimentally and configured within the fitness tracking device. Using the above described technique, a fitness tracking device may account for the extra work performed by a user when pushing a stroller or other object without requiring, for example, a heart rate sensor that could measure the increased load more directly.

Figure 9:
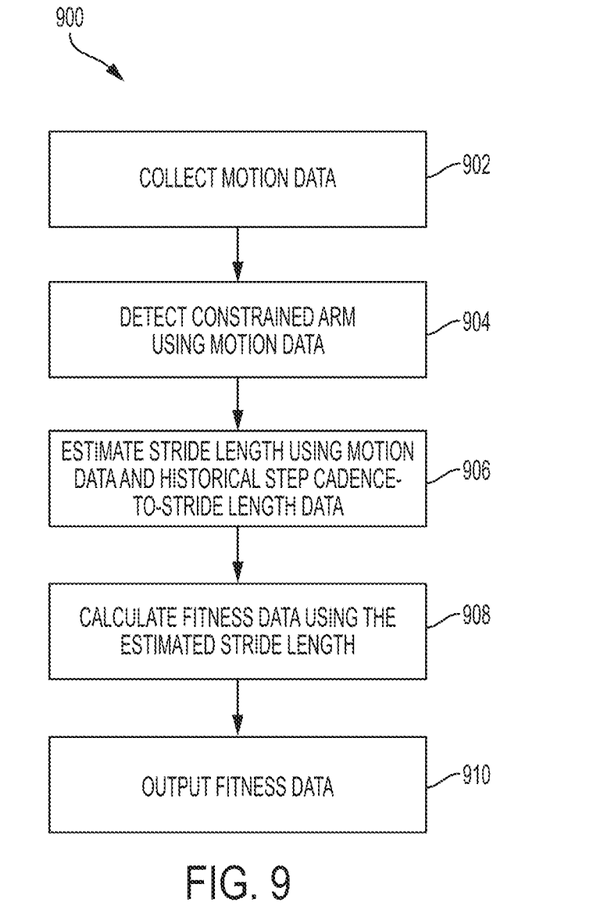
FIGS. 9 and 10 are flowcharts showing processing that may occur within a fitness tracking device and/or companion device, according to some embodiments of the present disclosure.

Referring to FIG. 9, a method 900 may be used to improve the accuracy of fitness data in the case where a user is wearing a fitness tracking device on an arm that is constrained. At block 902, motion data is collected using one or more motion sensors, such as an accelerometer, gyroscope, and/or GPS receiver. At block 904, the motion data is used to detect that the user's arm is constrained. In some embodiments, a constrained arm is detected using both a pose angle feature and an accelerometer energy feature. At block 906, the user's stride length is estimated using the motion data and historical step cadence-to-stride length data. The historical data may correspond to data collected for the user as part of a calibration process, or may correspond to data for a general population of users. At block 908, fitness data, such as distance, speed, caloric expenditure, and exercise minutes, is calculated using the estimated stride length. At block 910, the fitness data is output, for example, to a display module.

Figure 10:
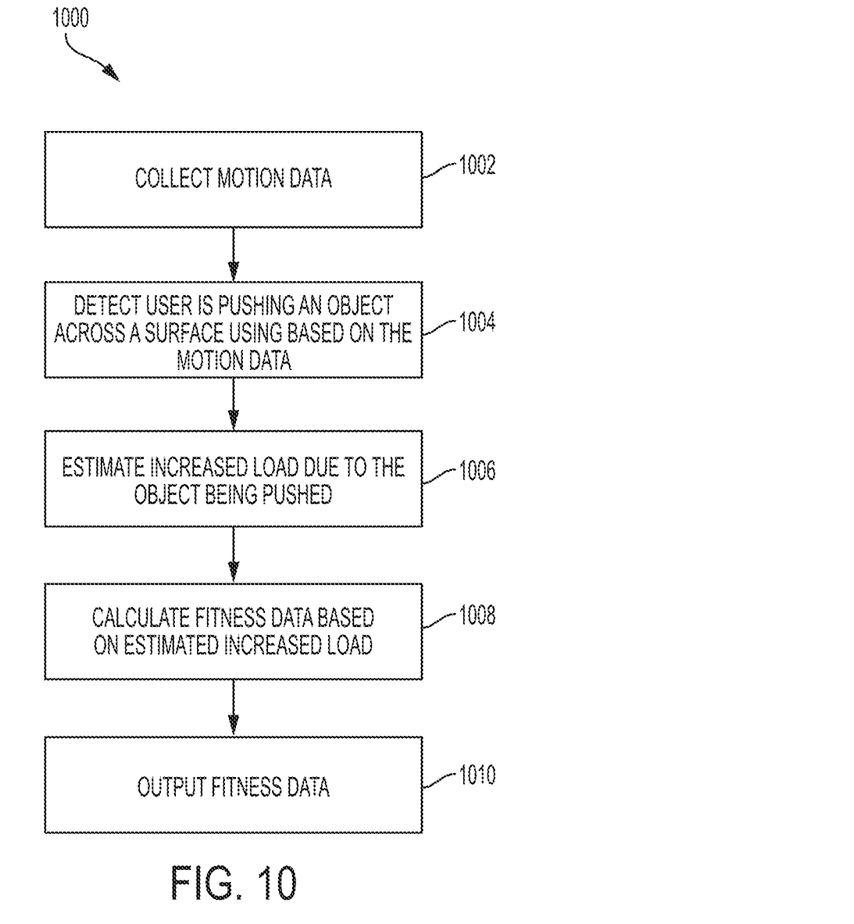

Referring to FIG. 10, a method 1000 may improve the accuracy of fitness data in the case where a user is user is pushing an object (e.g., a stroller) across a surface. At block 1002 and 1004, motion data is collected and used to detect that the user is pushing an object across a surface. In some embodiments, the detection includes using a road noise feature defined in terms of high and low frequency accelerometer energy. At block 1006, an estimate is made of the increased load due to the object being pushed. In one embodiment, the increased load may be estimated based on the weight and mechanics of a typical stroller. At block 1008, fitness data may be calculated taking into account the estimated increased load. At block 1010, the fitness data is output, for example, to a display module.

Methods described herein may represent processing that occurs within a fitness tracking (e.g., device 100 of FIG. 1) and/or within a companion device (e.g., device 300 of FIG. 3). The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, such as EPROM, EEPROM, flash memory device, or magnetic disks. The processor and the memory can be supplemented by, or incorporated in, special purpose logic circuitry.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method comprising:
    collecting motion data using a motion sensor worn on an arm of a user;
    calculating using the motion data, by a processor circuit in communication with the motion sensor, a pose angle of the arm of the user;
    detecting based on the pose angle and the motion data, by the processor circuit in communication with the motion sensor, an indication that the arm is constrained;
    in response to the detecting, estimating, by the processor circuit, a stride length of the user, the estimating comprising detecting a step cadence indicated by the motion data and selecting a historical stride length from historical step cadence-to-stride length data that matches the detected step cadence indicated by the motion data as the stride length;
    calculating, by the processor circuit, fitness data using the estimated stride length; and
    outputting the fitness data to the user.

2. The method of claim 1 wherein the calculating the fitness data comprises calculating at least one of distance traveled, speed, caloric expenditure, or exercise time.

3. The method of claim 1 wherein the detecting, based on the pose angle and the motion data, the indication that the arm is constrained comprises:
    determining an accelerometer energy based on the motion data; and
    detecting that the arm is constrained based on the pose angle and the accelerometer energy.

4. The method of claim 3 wherein the detecting that the arm is constrained based on the pose angle and the accelerometer energy comprises detecting that the arm is constrained when the pose angle is within a predetermined range of pose angles.

5. The method of claim 4 wherein the predetermined range of pose angles corresponds to pose angles greater than −45°.

6. The method of claim 1 wherein the estimating the stride length of the user comprises:
    obtaining a plurality of step cadence-to-stride length pairs;
    interpolating the plurality of step cadence-to-stride length pairs to generate a curve; and
    finding a point on the curve corresponding to a measured step cadence of the user.

7. The method of claim 6 wherein the obtaining the plurality of step cadence-to-stride length pairs comprises obtaining calibration data for the user.

8. The method of claim 6 wherein the obtaining the plurality of step cadence-to-stride length pairs comprises obtaining data for a general population of users.

9. The method of claim 1 comprising:
    detecting, by the processor circuit, that the user is pushing an object across a surface based on the motion data; and
    estimating, by the processor circuit, an increased load due to the object being pushed,
    wherein the calculating the fitness data comprises calculating the fitness data based on the estimated increased load.

10. The method of claim 9 where the detecting that the user is pushing the object across the surface comprises:
    calculating, by the processor circuit, road noise as a ratio of accelerometer data within a first frequency band to accelerometer energy within a second frequency band; and
    comparing, by the processor circuit, the road noise to a threshold value.

11. The method of claim 10 wherein the first frequency band comprises frequencies above 20 Hz and the second frequency band comprises frequencies below 4 Hz.

12. The method of claim 1, wherein the motion sensor comprises an accelerometer or a gyroscope.

13. A system comprising:
    a motion sensor configured to be located on an appendage of a user and configured to collect motion data; and
    a processor circuit coupled to the motion sensor and configured to execute instructions causing the processor circuit to:
        calculate, using the motion data, a pose angle of an arm of the user;
        detect, based on the pose angle and the motion data, an indication that the arm is constrained;
        in response to detecting the indication that the arm is constrained, estimate a stride length of the user, the estimating comprising detecting a step cadence indicated by the motion data and selecting a historical stride length from historical step cadence-to-stride length data that matches the detected step cadence indicated by the motion data as the stride length;
        calculate fitness data using the estimated stride length; and
        output the fitness data to the user.

14. The system of claim 13, wherein the instructions further cause the processor circuit to calculate at least one of distance traveled, speed, caloric expenditure, or exercise time.

15. The system of claim 13, wherein the instructions cause the processor circuit to detect, based on the pose angle and the motion data, the indication that the arm is constrained by causing the processor to:
    determine an accelerometer energy based on the motion data; and
    detect that the arm is constrained based on the pose angle and the accelerometer energy.

16. The system of claim 15 wherein the instructions further cause the processor circuit to detect that the arm is constrained based on the pose angle and the accelerometer energy when the pose angle is within a predetermined range of pose angles.

17. The system of claim 16 wherein the predetermined range of pose angles corresponds to pose angles greater than −45°.

18. The system of claim 13 wherein the instructions further cause the processor circuit to:
   obtain a plurality of step cadence-to-stride length pairs;
   interpolate the plurality of step cadence-to-stride length pairs to generate a curve; and
   estimate the stride length of the user by finding a point on the curve corresponding to a measured step cadence of the user.

19. The system of claim 18 wherein the instructions further cause the processor circuit to obtain the plurality of step cadence-to-stride length pairs from calibration data for the user.

20. The system of claim 18 wherein the instructions further cause the processor circuit to obtain the plurality of step cadence-to-stride length pairs from data for a general population of users.

21. The system of claim 13 wherein the instructions further cause the processor circuit to:
   detect that the user is pushing an object across a surface based on the motion data; and
   estimate an increased load due to the object being pushed, wherein the instructions further cause the processor circuit to calculate the fitness data based on the estimated increased load.

22. The system of claim 13, wherein the motion sensor comprises an accelerometer or a gyroscope.

* * * * *